United States Patent

Holmwood et al.

Patent Number: 4,518,600
Date of Patent: May 21, 1985

[54] COMBATING FUNGI WITH 1-PHENOXY-2-PYRIMIDINYL ALKANOLS

[75] Inventors: Graham Holmwood, Wuppertal; Paul-Ernst Frohberger, Leverkusen; Wilhelm Brandes, Leichlingen; Volker Paul, Solingen, all of Fed. Rep. of Germany

[73] Assignee: Bayer Aktiengesellschaft, Leverkusen, Fed. Rep. of Germany

[21] Appl. No.: 161,636

[22] Filed: Jun. 20, 1980

Related U.S. Application Data

[63] Continuation of Ser. No. 937,650, Aug. 28, 1978, abandoned.

[30] Foreign Application Priority Data

Sep. 20, 1977 [DE] Fed. Rep. of Germany ....... 2742173

[51] Int. Cl.$^3$ ................. A61K 31/505; C07D 239/26
[52] U.S. Cl. ..................................... 514/256; 544/334; 544/335; 546/339; 546/345; 424/263
[58] Field of Search ................. 544/335; 424/251

[56] References Cited

U.S. PATENT DOCUMENTS

| | | | |
|---|---|---|---|
| 3,085,938 | 4/1963 | Berger et al. | 546/344 |
| 3,515,788 | 6/1970 | Edenhofer et al. | 424/263 |
| 3,818,009 | 6/1974 | Taylor et al. | 544/335 |
| 3,819,702 | 6/1974 | Lafon | 544/335 |
| 3,869,456 | 3/1975 | Taylor et al. | 424/251 |
| 4,020,071 | 4/1977 | Raabe et al. | 544/335 |
| 4,039,675 | 8/1977 | Krumkalns | 424/263 |
| 4,043,790 | 8/1977 | Krumkalns | 71/94 |

Primary Examiner—Glennon H. Hollrah
Assistant Examiner—James H. Turnipseed
Attorney, Agent, or Firm—Sprung Horn Kramer & Woods

[57] ABSTRACT

1-Phenoxy-2-pyridinyl(pyrimidinyl)-alkanols of the formula

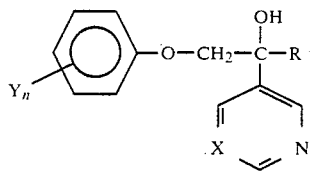

in which

R represents alkyl, optionally substituted aryl or optionally substituted aralkyl, X represents a nitrogen atom or the CH group, Y represents halogen, alkyl, cycloalkyl, alkoxy, halogenoalkyl, alkylthio, or an optionally substituted phenyl, phenoxy, phenylalkoxy or phenylalkyl radical, and n represents 0 or an integer from 1 to 5, the Y's being selected independently of one another when n is 2, 3, 4 or 5, in the form of the free base, a salt or a metal salt complex thereof, which possess fungicidal properties.

7 Claims, No Drawings

COMBATING FUNGI WITH 1-PHENOXY-2-PYRIMIDINYL ALKANOLS

This is a continuation of application Ser. No. 937,650, filed Aug. 28, 1978 now abandoned.

The present invention relates to and has for its objects the provision of particular new 1-phenyl-2-pyridinyl(pyrimidinyl)-alkanols which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that certain trityl-1,2,4-triazoles, such as triphenyl-(1,2,4-triazol-1-yl)methane, possess a good fungicidal activity (see DT-OS (German Published Specification) No. 1,795,249). Their action, however, is not always entirely satisfactory, especially if low amounts and low concentrations are used. Furthermore, it has been generally known for a considerable time that zinc ethylene-1,2-bis-dithiocarbamate is a good agent for combating fungal diseases of plants (see Phytopathology 33, 1113 (1963)). However, its possible use as seed dressings is limited, since its activity is low if low amounts and low concentrations are used.

The present invention now provides, as new compounds, the phenoxy-pyridinyl(pyrimidinyl)-alkanols of the general formula

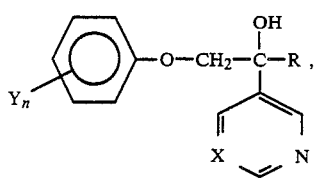

in which
R represents alkyl, optionally substituted aryl or optionally substituted aralkyl,
X represents a nitrogen atom or the CH group,
Y represents halogen, alkyl, cycloalkyl, alkoxy, halogenoalkyl, alkylthio, or an optionally substituted phenyl, phenoxy, phenylalkoxy or phenylalkyl radical and
n represents 0 or an integer from 1 to 5, the Y's being selected independently of one another when n is 2, 3, 4 or 5, in the form of the free bases, their acid addition salts and metal complexes, especially the salts and complexes that are physiologically tolerated. The present compounds exhibit powerful fungicidal properties.

Preferably, R represents straight-chain or branched alkyl with 1 to 4 carbon atoms, optionally substituted aryl with 6 to 10 carbon atoms (especially phenyl) or optionally substituted aralkyl with 6 to 10 carbon atoms in the aryl part and up to 4 carbon atoms in the alkyl part (especially benzyl), the substituents in either case being halogen (especially fluorine, chlorine or bromine), straight-chain or branched alkyl with 1 to 4 carbon atoms, cycloalkyl with 5 to 7 carbon atoms (especially cyclohexyl), halogenoalkyl with up to 2 carbon atoms and up to 5 identical or different halogen atoms (especially fluorine and chlorine atoms), alkoxy or alkylthio with up to 2 carbon atoms or optionally substituted phenyl, optionally substituted phenoxy or optionally substituted phenylalkoxy or optionally substituted phenylalkyl, in either case with 1 or 2 carbon atoms in the alkyl part, the substituents on each phenyl part being halogen (especially fluorine, chlorine or bromine) or alkyl with up to 4 carbon atoms;

Y represents halogen (especially fluorine, chlorine or bromine), straight-chain or branched alkyl with 1 to 4 carbon atoms, cycloalkyl with 5 to 7 carbon atoms (especially cyclohexyl), halogenoalkyl with up to 2 carbon atoms and up to 5 identical or different halogen atoms (especially fluorine and chlorine atoms), alkoxy or alkylthio with up to 2 carbon atoms or optionally substituted phenyl, optionally substituted phenoxy, optionally substituted phenylalkoxy or optionally substituted phenylalkyl, in either case with 1 or 2 carbon atoms in the alkyl part, the substituents on each phenyl part being halogen (especially fluorine, chlorine or bromine) or alkyl with up to 4 carbon atoms; and
n represents 0, 1, 2 or 3.

Of special interest are such compounds of the general formula (I), in which X represents a CH-group. Of these compounds of formula (I), in which X represents an N-atom, such compounds are of special interest, in which Y represents optionally substituted phenyl, phenoxy, phenoxyalkyl or phenylalkyl.

The compounds of the formula (I) possess an asymmetrical carbon atom; they can therefore be present as the two optical isomers or as the racemate. Formula (I) is intended to embrace all the isomers.

Surprisingly, the phenoxy-pyridinyl(pyrimidinyl)alkanols according to the invention exhibit a substantially greater fungicidal activity, especially against species of mildew, than the trityl-1,2,4-triazoles known from the prior art, such as triphenyl-(1,2,4-triazol-1-yl)-methane, and than the known zinc ethylene-1,2-bis-dithiocarbamate, which are compounds of the same type of action. The active compounds according to the invention thus represent an enrichment of the art.

The present invention also provides a process for the preparation of a phenoxy-pyridinyl(pyrimidinyl)-alkanol of the formula (I), or an acid addition salt or metal complex thereof, in which a phenoxy-ketone of the general formula

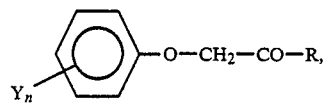

in which R, Y and n have the above-mentioned meanings, is reacted with a pyridinyl halide or pyrimidinyl halide of the general formula

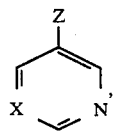

in which
Z represents halogen, preferably chlorine or bromine, and
X has the above-mentioned meaning, in the presence of a diluent and in the presence of an alkali metal-organic compound and, if required, an acid or a metal salt is subsequently added on.

If 1-(4-chlorophenoxy)-3,3-dimethylbutan-2-one and 3-bromopyridine, in the presence of n-butyl-lithium, are used as starting materials, the course of the reaction can be represented by the following equation:

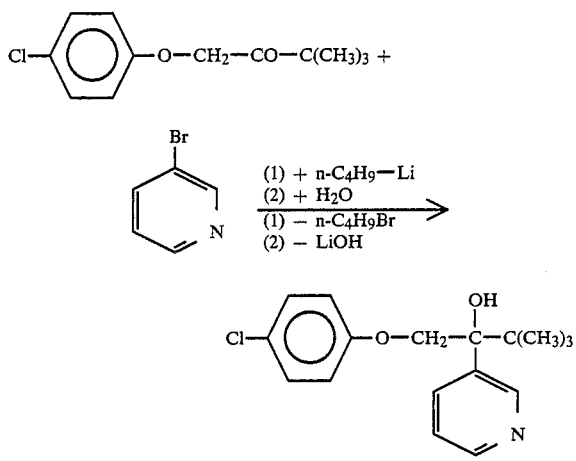

The starting materials of the formula (II) are known (see DT-OS (German Published Specification) No. 2,105,490 and DT-OS (German Published Specification) No. 2,201,063) and can be prepared easily in accordance with the processes described there. They are obtained, for example, by reacting appropriate phenols with appropriate halogenoketones in the presence of an acid-binding agent and of a diluent.

The halides of the formula (III) are generally known compounds of organic chemistry.

Preferred diluents for the reaction according to the invention are inert organic solvents, especially those which have a low solidification point, particularly ethers, such as diethyl ether or tetrahydrofuran. Preferably, mixtures of these two ethers are used.

The preferred alkali metal-organic compounds employed in the reaction according to the invention are alkali metal-alkyls, such as n-butyl-lithium, although alkali metal-aryls, such as phenyl-lithium, can also be employed.

The reaction temperatures in the process according to the invention can be varied within a certain range. In general, the reaction is carried out at from $-150°$ C. to $-50°$ C., preferably at from $-120°$ C. to $-80°$ C.

The reaction according to the invention is preferably carried out under an inert gas such as, in particular, nitrogen or argon.

In carrying out the process according to the invention, the phenoxyketone of the formula (II) and the halide of the formula (III) are preferably employed in substantially equimolar amounts; however, it is possible to use up to 20 mol percent less or more than the equimolar amount. The alkali metal-organic compound is advantageously used in an excess of 5 to 75 mol percent, preferably of 10 to 50 mol percent. A possible procedure is first to allow the alkali metal-organic compound to react with the halide of the formula (III) and then to add the keto compound of the formula (II); however, it is also possible first to introduce the keto compound and the halide and then to add the alkali metal-organic compound at a low temperature (for example at $-100°$ to $-130°$ C.).

The compounds of the formula (I) are isolated by hydrolyzing the alkali metal alkanolate (for example lithium alkanolate), first formed in the reaction, with water. The further working up then takes place in the usual manner.

All physiologically tolerated acids can be used to prepare acid addition salts of the compounds of the formula (I), especially the hydrogen halide acids (for example hydrobromic acid and especially hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner in accordance with customary methods of forming salts, for example by dissolving a compound of the formula (I) in a suitable inert solvent and adding the acid, for example hydrochloric acid, and can be isolated in a known manner, for example by filtering off, and be purified, if appropriate, by washing with an inert organic solvent.

To prepare metal salt complexes of the compounds of the formula (I), it is preferred to use salts of metals of main groups II to IV and of sub-groups I, II and IV to VIII of the Periodic Table; copper, zinc, manganese, magnesium, tin, iron and nickel may be mentioned as examples of these. Suitable anions of the salts are those derived from physiologically tolerated acids, especially the hydrogen halide acids (for example hydrochloric acid and hydrobromic acid), phosphoric acid, nitric acid and sulphuric acid.

The metal salt complexes of the compounds of the formula (I) can be obtained in a simple manner in accordance with customary processes, for example by dissolving the metal salt in an alcohol, for instance ethanol, and adding to the compound of the formula (I). Metal salt complexes can be isolated in a known manner, for example by filtering off, and can optionally be purified by recrystallizing.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens. They display a particularly good activity against parasitic fungi on above-ground parts of plants.

As plant protection agents, the active compounds according to the invention can be used particularly successfully for combating powdery mildew fungi, for example for combating powdery mildew of apple (*Podosphaera leucotricha*) and powdery mildew of cereals, as well as against other diseases of cereals; furthermore, they can in particular be used for combating the fungi Pyricularia and Pellicularia.

The partially systemic action of the compounds should be singled out particularly. Thus it proves possible to protect plants against fungal attack if the active compound is supplied to the above-ground parts of the plant via the soil and the root.

As plant protection agents, the active compounds according to the invention can be used for the treatment of seed or of soil and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. Where water is used as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, rematicides, herbicides, bird repellants, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.001 percent.

In the treatment of seed, amounts of active compound of 0.001 to 50 g, preferably 0.01 to 10 g, per kilogram of seed are generally employed.

For the treatment of soil, amounts of active compound of 1 to 1,000 g, especially 10 to 200 g, are generally employed per cubic meter of soil.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention The process for preparing the novel compounds is shown in the following illustrative examples:

EXAMPLE 1

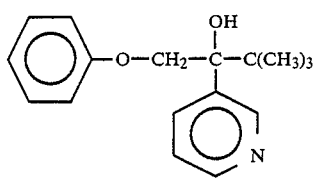

50 ml of a 15% strength solution of n-butyl-lithium (containing about 0.12 mol) in n-hexane were slowly added dropwise, under a dry nitrogen atmosphere, to a solution, cooled to −110° C., of 12.6 g (0.1 mol) of bromopyridine in 150 ml of a 2:1 mixture of absolute tetrahydrofuran and absolute ether. After completion of the addition, the reaction mixture was allowed to warm up to −80° C., and was stirred at this temperature for a further 10 minutes and then cooled to −110° to −120° C. At this temperature, a solution of 19.2 g (0.1 mol) of 3,3-dimethyl-1-phenoxy-butan-2-one in 80 ml of absolute tetrahydrofuran was added dropwise. The mixture was then stirred overnight at −78° C. Thereafter it was allowed to warm up to room temperature, and 200 ml of ether were added.

The reaction mixture was extracted three times with 1N hydrochloric acid. The combined hydrochloric acid extracts were washed with ether, poured onto solid sodium bicarbonate and repeatedly extracted with ethyl acetate. The ethyl acetate solution was washed with water, dried over sodium sulphate and concentrated. The residue was recrystallized from cyclohexane. 15 g (55% of theory) of 3,3-dimethyl-1-phenoxy-2-pyridin-3-yl-butan-2-ol of melting point 89°–90.5° C. were obtained.

EXAMPLE 2

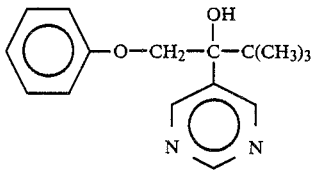

A solution of 19.2 g (0.1 mol) of 3,3-dimethyl-1-phenoxy-butan-2-one in 110 ml of absolute tetrahydrofuran and 70 ml of absolute ether was cooled to −120° C. under a dry nitrogen atmosphere. A solution of 15.7 g (0.1 mol) of 5-bromopyrimidine in 50 ml of absolute tetrahydrofuran was added dropwise. 60 ml of a 15% strength solution of n-butyl-lithium (containing about 0.14 mol) in n-hexane were then slowly added dropwise at −120° C. The mixture was stirred further, first for 2 hours at a temperature of about −110° C. and then overnight at −78° C. The reaction mixture was then warmed to room temperature, mixed with 100 ml of 10% strength ammonium chloride solution and concentrated in vacuo. The aqueous suspension was then extracted with ethyl acetate. The ethyl acetate extract was washed successively twice with 1N hydrochloric acid, twice with water and once with saturated sodium chloride solution, dried over sodium sulphate and concentrated. The residue was recrystallized from cyclohexane. 10.5 g (39% of theory) of 3,3-dimethyl-1-phenoxy-2-pyrimidin-5-yl-butan-2-ol of melting point 127°–129° C. were obtained.

The following compounds of the general formula

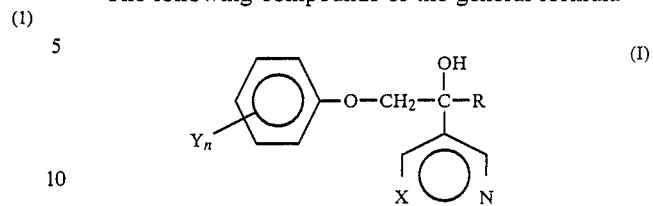

were obtained analogously:

TABLE

| Compound No. | $Y_n$ | X | R | Melting Point (°C.) |
|---|---|---|---|---|
| 3 | 2-CH₃ | CH | C(CH₃)₃ | 66–68 |
| 4 | 2,4-Cl₂ | CH | C(CH₃)₃ | 113.5–115 |
| 5 | 4-Br | CH | C(CH₃)₃ | 171–173 |
| 6 | 4-OCH₃ | CH | C(CH₃)₃ | 178–180 |
| 7 | 4-Cl | CH | C(CH₃)₃ | 162–164 |
| 8 | 4-CH₃ | CH | C(CH₃)₃ | 131–133 |
| 9 | 2-CH₃,4-Cl | CH | C(CH₃)₃ | 127–128 |
| 10 | 4-F | CH | C(CH₃)₃ | 120–121 |
| 11 | 3,4-Cl₂ | CH | C(CH₃)₃ | 125–126.5 |
| 12 | 3-CF₃ | CH | C(CH₃)₃ | 132–133.5 |
| 13 | 4-O—CH₂—C₆H₅ | CH | C(CH₃)₃ | 125–126 |
| 14 | 2-OCH₃,4-Cl | CH | C(CH₃)₃ | 128–129 |
| 15 | 4-C₆H₅ | CH | C(CH₃)₃ | 120–121 |
| 16 | 2,4-Cl₂ | CH | C₆H₅ | >238 (decomposition) (×½NDS) |
| 17 | — | CH | C₆H₅ | 194–197 (×½NDS) |
| 18 | 4-Cl | CH | C₆H₅ | 182–185 (×½NDS) |
| 19 | 4-Cl | CH | 2,6-Cl₂-C₆H₃ | >250 (×½NDS) |
| 20 | 2-CH₃,4-Cl | CH | C₆H₅ | 187–190 (×½NDS) |
| 21 | 3-CF₃ | CH | C₆H₅ | 238–240 (×½NDS) |
| 22 | 4-OCH₃ | CH | C₆H₅ | 175–177 (×½NDS) |
| 23 | 2,4-Cl₂ | CH | CH₃ | 98.5–100 |
| 24 | — | CH | CH₃ | 204–208 (×½NDS) |
| 25 | 4-CH₃ | CH | CH₃ | 184–186 (×½NDS) |
| 26 | 4-OCH₃ | CH | CH₃ | 200–203 (×½NDS) |
| 27 | 4-Cl | N | C(CH₃)₃ | 172–174 |
| 28 | 4-F | N | C(CH₃)₃ | 163.5–164.5 |
| 29 | 3,4-Cl₂ | N | C(CH₃)₃ | 155–157 |
| 30 | 4-CH₃ | N | C(CH₃)₃ | 152–153.5 |

TABLE-continued

| Compound No. | $Y_n$ | X | R | Melting Point (°C.) |
|---|---|---|---|---|
| 31 | 4-O—CH$_2$—  | N | C(CH$_3$)$_3$ | 122–124 |
| 32 | 2,4-Cl$_2$ | N | C(CH$_3$)$_3$ | 96–99 |
| 33 | — | N |  | |
| 34 | 4-O—  | CH | C(CH$_3$)$_3$ | 103–104° C. |
| 35 | 4-F | CH |  | 222–225° C. (×½NDS) |
| 36 | 4-CH$_3$O | N | —C(CH$_3$)$_3$ | 136–137 |
| 37 | 2,4-Cl$_2$ | CH |  | viscous oil |

Note: NDS = 1,5-naphthalenedisulphonic acid

The fungicidal activity of the compounds of this invention is illustrated by the following examples wherein the compounds according to the present invention are each identified by the number (given in brackets) from the preparative examples hereinabove.

EXAMPLE 3

Powdery mildew of barley (*Erysiphe graminis* var. *hordei*) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. *hordei* and grown on at 21° to 22° C. and 80–90% relative atmospheric humidity and 16 hours' exposure to light. The typical mildew pustules formed on the leaves over the course of 6 days.

The active compounds, active compound concentrations in the seed dressing, the amount of dressing used and the percentage infection with mildew were recorded. In this test compound (3) showed a very good action which was distinctly superior to the compounds known from the prior art:

EXAMPLE 4

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21° to 22° C. and 80–90% atmospheric humdity the occurrence of mildew pustules on the plants was evaluated.

The active compounds, active compound concentrations in the spray liquor and degrees of infection were recorded. In this test compounds (3), (4), (9) and (27) showed a very good action, which was distinctly superior to that of the compounds known from the prior art.

EXAMPLE 5

Podosphaera test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated by dusting the conidia of the apple powdery mildew causative organism (*Podosphaera leucotricha*) and placed in a greenhouse at a temperature of 21° to 23° C. and at a relative atmospheric humidity of about 70%. 10 days after the inoculation, the infection of the seedlings was determined.

The active compounds, active compound concentrations and results were recorded. In this test compounds (3), (4), (9) and (27) show a very good action, which is distinctly superior to that of the compounds known from the prior art.

EXAMPLE 6

Mycelium growth test

Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Composition of the solvent mixture:
  0.19 part by weight of acetone or DMF
  0.01 part by weight of emulsifier (alkylaryl polyglycol ether)
  1.80 parts by weight of water
Ratio of solvent mixture to nutrient medium:
  2 parts by weight of solvent mixture
  100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of organisms stated in the table and incubated at about 21° C.

Evaluation was carried out after 4–10 days, dependent upon the speed of growth of the organisms. When evaluation was carried out the radial growth of the organism on the treated nutrient media was compared with the growth on the control nutrient medium.

The active compounds, the active compound concentrations and the results were recorded. In this test compounds (3), (4), (9) and (27) showed a very good action, which was distinctly superior to that of the compounds known from the prior art.

EXAMPLE 7

Pyricularia and Pellicularia test

Solvent: 11.75 parts by weight of acetone
Dispersing agent: 0.75 parts by weight of alkylaryl polyglycol ether
Water: 987.50 parts by weight The amount of active compound required for the desired concentration of active compound in the spray liquid was mixed with the stated amount of the solvent and of the dispersing agent and the concentrate was diluted with the stated amount of water.

Rice plants about 2–4 weeks old were sprayed with the spray liquid until dripping wet. The plants remained in a greenhouse at temperatures of 22° to 24° C. and a relative atmospheric humidity of about 70% until they were dry. Thereafter, the plants were inoculated with an aqueous suspension of 100,000 to 200,000 spores/ml of *Pyricularia oryzae* and placed in a chamber at 24° to 26° C. and 100% relative atmospheric humidity.

Other rice plants, which had been sprayed and dried in the above-described manner, were infected with a culture of *Pellicularia sasakii* grown on malt agar and were set up at 28° to 30° C. and 100% relative atmospheric humidity.

5 to 8 days after the inoculation, the infection of all the leaves present at the time of inoculation with *Pyricularia oryzae* was determined as a percentage of the untreated but also inoculated control plants.

In the case of the plants with *Pellicularia sasakii*, the infection at the leaf sheaths after the same time was determined, again in relation to the untreated but infected control.

The active compounds, the active compound concentrations and the results were recorded. In this test compounds (3), (4) and (9) showed a very good action, which was distinctly superior to that of the compounds known from the prior art.

It will be appreciated that the instant specification and examples are set forth by way of illustration and not limitation, and that various modifications and changes may be made without departing from the spirit and scope of the present invention.

What we claim is:

1. A 1-phenoxy-2-pyrimidinyl-alkanol of the formula

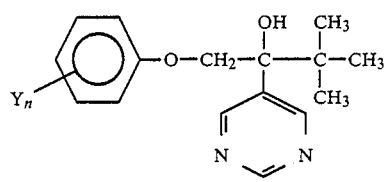

in which
Y is fluorine, chlorine, methyl, methoxy or benzyloxy, and
n is 0, 1 or 2.

2. A compound according to claim 1, wherein such compound is 3,3-dimethyl-1-p-chlorophenoxy-2-pyrimidin-5-yl-butan-2-ol of the formula

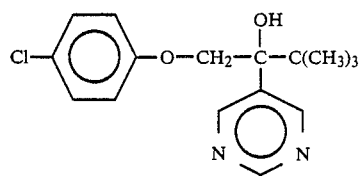

3. A compound according to claim 1, wherein such compound is 3,3-dimethyl-1-p-fluorophenoxy-2-pyrimidin-5-yl-butan-2-ol of the formula

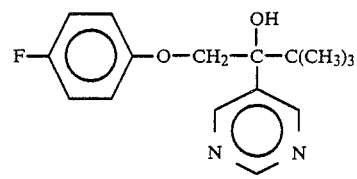

4. A compound according to claim 1, wherein such compound is 3,3-dimethyl-1-p-tolyloxy-2-pyrimidin-5-yl-butan-2-ol of the formula

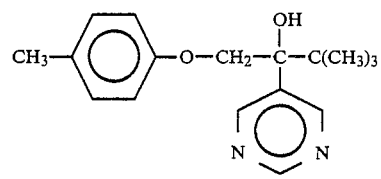

5. A fungicidal composition containing as active ingredient a fungicidally effective amount of a compound according to claim 1 in admixture with a diluent.

6. A method of combating fungi which comprises applying to the fungi, or to a habitat thereof, a fungicidally effective amount of a compound according to claim 1.

7. The method according to claim 6, wherein such compound is
3,3,-dimethyl-1-p-chlorophenoxy-2-pyrimidin-5-yl-butan-2-ol,
3,3-dimethyl-1-p-fluorophenoxy-2-pyrimidin-5-yl-butan-2-ol, or
3,3-dimethyl-1-p-tolyloxy-2-pyrimidin-5-yl-butan-2-ol.

* * * * *